(12) United States Patent
Kwirandt

(10) Patent No.: US 8,600,148 B2
(45) Date of Patent: Dec. 3, 2013

(54) INSPECTION DEVICE

(75) Inventor: Rainer Kwirandt, Barbing (DE)

(73) Assignee: Krones AG (DE)

( * ) Notice: Subject to any disclaimer, the term of this patent is extended or adjusted under 35 U.S.C. 154(b) by 382 days.

(21) Appl. No.: 12/647,141

(22) Filed: Dec. 24, 2009

(65) Prior Publication Data

US 2010/0158344 A1 Jun. 24, 2010

(30) Foreign Application Priority Data

Dec. 24, 2008 (DE) .................. 10 2008 063 077

(51) Int. Cl.
G06K 9/00 (2006.01)

(52) U.S. Cl.
USPC ............. 382/142; 356/237.6; 356/240.1; 250/223 B

(58) Field of Classification Search
USPC ......... 382/142; 250/559.45; 356/237.2–237.6
See application file for complete search history.

(56) References Cited

U.S. PATENT DOCUMENTS

| | | | | |
|---|---|---|---|---|
| 3,035,380 A | * | 5/1962 | Leavens | 53/458 |
| 3,545,610 A | * | 12/1970 | Leonard et al. | 209/579 |
| 4,625,107 A | | 11/1986 | Planke | 250/223 |
| 4,972,494 A | * | 11/1990 | White et al. | 382/143 |
| 6,031,221 A | | 2/2000 | Furnas | 250/223 |
| 6,618,495 B1 | | 9/2003 | Furnas | 382/142 |
| 7,331,152 B2 | * | 2/2008 | Menke | 53/67 |
| 2004/0057046 A1 | * | 3/2004 | Abbott et al. | 356/239.1 |

FOREIGN PATENT DOCUMENTS

| | | | | |
|---|---|---|---|---|
| DE | 296 18 394 | 11/1997 | | G01N 21/90 |
| DE | 199 04 732 | 9/1999 | | G01N 21/90 |
| DE | 101 34 714 | 2/2003 | | B07C 5/342 |
| DE | 103 22 459 | 11/2004 | | G01N 21/90 |
| DE | 20 2005 006 220 | 7/2005 | | G01N 21/88 |
| EP | 1 477 794 | 11/2004 | | G01N 21/90 |
| EP | 1 600 764 | 11/2005 | | G01N 21/90 |
| EP | 1 985 997 | 10/2008 | | G01N 21/90 |
| GB | 2 334 576 | 6/1999 | | G01N 21/90 |

OTHER PUBLICATIONS

German Search Report issued in DE 10 2008 063 077.2, received Dec. 2, 2011 (4 pgs).

* cited by examiner

*Primary Examiner* — Roy M Punnoose
*Assistant Examiner* — Isiaka Akanbi
(74) *Attorney, Agent, or Firm* — Hayes Soloway P.C.

(57) ABSTRACT

A device for inspecting the external surfaces of containers using a radiation device which directs light onto a container to be inspected. The device includes a transport device for transporting the container with respect to the radiation device, and an image capturing device which captures the container illuminated by the radiation device, with a background being located behind the container with respect to the image capturing device, with respect which the container can be imaged. The background has both a lighter area and a darker area by comparison with this lighter area.

23 Claims, 3 Drawing Sheets

INSPECTION DEVICE

BACKGROUND OF THE INVENTION

The present invention relates to an inspection device and in particular to an inspection device for containers. It is customary in the field of the beverage processing industry to inspect not only the filled containers or containers to be filled themselves, but also the labels attached to these containers. Thus, such labels might have faults such as warpages, tears or the like, which are intended to be detected in this way.

In this context, inspection devices are known from the prior art, wherein the containers to be inspected are transported on a conveyor belt and are inspected from several sides for example by means of deflection mirrors. Particular problems are encountered here in the case of so-called metallic labels, which generate desired reflections which are partially erased (unintentionally) while being monitored through polarising filters.

A container inspection machine is known from DE 199 04732 A1. Here, the containers to be inspected are carried on a conveyor belt and are monitored by means of CCD cameras. Further, light sources are provided which illuminate the containers from the back side with regard to the CCD camera.

DE 103 22 459 B3 describes an inspection device for bottles. In these devices, the bottles are illuminated from above by means of illumination devices, and cameras monitor the containers from the side or transversely to the bottle axis. Also, a light image background is used, in order to be able to generate an advantageous image of the bottle compared thereto.

DE 20 2005 006 220 U1 describes an inspection device for inspecting closed containers. Here, a housing is provided, within which an illumination device and cameras are disposed.

It is also known to equip the entire internal space in a homogenous way, in order to provide a diffuse illumination of the inspection space, with a great emphasis being put on the optical properties with respect to reflection and diffusion. It is also known to adapt the characteristics of the transport device correspondingly, in order to achieve in this way that all of the surfaces of the housing and inside the housing radiate light onto the container to be inspected, so that all of these surfaces inside the housing are used as a source of illumination.

During image capturing, however, the problem arises that the containers are not always in the same position relative to the conveyor belt, and therefore differences in the captured image may occur from one bottle to another. In the prior art, however, these positioning inaccuracies of the containers are not addressed in more detail. The known devices always assume an ideal position of the container, which is not a realistic assumption in view of processing rates as high as 50,000 containers or more per hour.

In real-life systems, the containers are not always exactly in the same position in the transport direction and laterally thereto. In the transport direction, each system has some delay and some jitter. If, for example, a delay of one millisecond is assumed, which is a typical value, and if a conveying speed of two meters per second is used as a basis, then this may result in deviations in the order of two millimeters. If one additionally assumes that, during braking and accelerating of the conveyor belt, some slipping of the containers relative to the conveyor belt may occur, then this may result in overall positional inaccuracies in the order of 5 mm.

Also, the lateral position relative to the transfer direction is not precise. If, for example, a conveyor clearance of approx. 10 mm is assumed, the lateral position relative to the direction of travel may vary by up to 5 mm. This will cause substantial interferences to the inspection task. If, for example, it is also assumed that a camera inspects a range of 300 mm and is positioned at a distance of 600 mm from the object, with four cameras being offset from each other by 90°, respectively, then 300 mm will be projected onto approx. 600 pixels, i.e. 0.5 mm correspond to 1 pixel.

If a container is displaced by e.g. 5 mm in the transport direction, the distance to a camera will be increased by 3.5 mm and the distance to a further camera will be reduced by 3.5 mm. As a result, an imaging error may occur at the interface from −4 pixels in the case of one camera and +3 pixels in the case of the other. If the four views are to be equalised and to be merged into one overall sequence, an imaging error of 7 pixels relative to 600 pixels will occur at the interface between the two cameras. This error will be visible most of all in the edge regions of the camera.

Apart from the imaging changes, the lateral offset in the camera image is of importance. The correction mask no longer coincides with the theoretically ideal position and areas will be evaluated with incorrect elongation factors, i.e. the error may integrally propagate.

For these reasons it is of advantage to know the actual position of the container. To this end, in the simplest scenario, the contour of the container will at least partially be determined. To this end, however, there must be a contrast between the contour and the background. It is therefore necessary to localise exactly the bottle edges in the captured images, which is in principle possible by using software solutions, provided that a sufficient contrast is present. Further, due to the curvatures of the bottles towards the sides of the bottles, the distortion of the labels in the image increases. Thus, in order to achieve an advantageous correction of the image, an exact localization of the bottle contour is required. Often, however, the labels have not been attached to the bottles around the entire circumference thereof, so that the bottle contour has to be determined also in places where no label is attached. If darker bottles are used, it is possible to use a correspondingly light background, in order to achieve an exact localization of the position of the containers. If lighter bottles are used, a darker background could be used, in order to facilitate the localization of the bottles in this case. If, however, different bottles are used, their backgrounds need to be changed, in order to create the respective contrast against the background in each case.

As mentioned above, in the prior art the housings are either completely black or are illuminated in a homogenous, diffuse and light manner. In the case of black housings, only the contours of light, milky containers may be detected, not those of dark containers or those with products such as cola or red wine or those of a dark beer bottle.

Conversely, if light housings are used, only the contours of dark containers may be detected, the contours of clear, light containers containing a clear, light product, such as e.g. water in white glass, water in disposable PET, possibly even milk in white glass or similar can not be detected. The contrasts are not sufficient for a determination of the contour to be carried out. In this case, at least the housing would have to be replaced in each case, if both light and dark products are to be inspected.

SUMMARY OF THE INVENTION

The present invention is therefore based on the object of allowing different bottles and in particular also differently light bottles to be monitored with little effort. In particular, a solution is to be provided which avoids complex conversions.

An apparatus according to the invention for inspecting the external surfaces of containers includes a radiation device directing light onto a container to be inspected. Further, a transport device is included, which transports the container with respect to the radiation device, as well as an image capturing device which captures at least one image of the container illuminated by the radiation device, with a background being disposed behind the container with respect to the image capturing device, with respect to which the container may be imaged. In this way, the image capturing device detects the radiation directed by the radiation device onto the container and reflected (in particular scattered) from this container.

According to the invention, the background has at least one lighter area and at least one darker area by comparison to this lighter area, preferably, however, two dark areas if viewed by means of an image detection device (camera), namely the lighter area behind a viewed container and the darker areas to the right and the left adjacent to it, in order to obtain in the case of light containers clearly defined contours on both sides.

Thus, the viewing range of a housing opposite the image capturing device is designed to be at least partially light. In this case, the question of the optical properties is of secondary importance and in particular no preferred reflection and diffusion properties need to be present. It is sufficient to be able to detect the contour of the darker containers. The lighter area may for example have a colour or may also be white.

The containers to be inspected are in particular, but not exclusively, glass or plastic bottles, which have already been provided with labels. The external surface of the container is understood to mean in particular the external surface of the container, which is provided with a label. The radiation reflected from the container is understood to mean in particular a scattered radiation. Any capturing of reflected radiation is preferably avoided. The positioning of the background behind the container is understood to mean in particular the geometrical area behind the container, which may be detected by the image capturing device or the camera, if necessary also in a sequence of refraction and/or diffraction effects on the container.

Preferably, the background has a section of contrast, in which the lighter area merges into the darker area. The section of contrast may for example be an edge or a line, in which a lighter, in particular white area may merge into a darker, in particular black area.

Preferably, the area of the background, which is located behind the container in the viewing direction of the image capturing device, is a lighter area. This means that along a straight line which extends from the image capturing device through the longitudinal axis of the container, a lighter area is disposed behind the container. By this means it may be achieved that the area behind the bottle is light, so that a good possibility is provided to create a contrast between dark bottles and the background.

When looking at the beam path through a clear bottle containing a clear liquid, it will be seen that the beam path will be severely refracted through this filled bottle, even to such an extent that beams will intersect each other immediately behind the bottle. Here, in particular, the beam paths extending along the contour of the bottle are widely deflected.

The concept forming the basis of the invention is to dispose the darker areas in such a way that the light emitting therefrom can still be seen when monitoring the bottle. Thus, the image capturing device can see even darker or black parts of the background which are far away, and in this way the bottle contour will become black and will thus be readily visible before the lighter background. Thus, it becomes possible to detect the contour of the bottle. Preferably, here, the darker areas of the background are displaced by approx. 45° relative to the respective viewing direction.

In a further advantageous embodiment, a transition or the section of contrast between a lighter area and a darker area of the background extends essentially vertically. In this way, a particularly exact determination of the bottle contour or the position of the bottle may be carried out. The term "essentially vertical" is understood to include also trajectories which deviate from the vertical direction by less than 10°.

In a further advantageous embodiment, a darker area of the background will in each case follow a lighter area of the background on both sides. In this way, the two sides of the bottle or the edge contours may be established. However, it would also be possible to provide only one area of contrast, for example, when the diameter of the bottle is known, and in this way a location of contrast or a lateral edge may be used as the basis for calculating the second location of contrast or the further lateral edge. In this advantageous embodiment, the dark area mentioned is thus visible due to the refraction only in the case of lighter containers. In the case of darker containers containing a dark liquid, no beams will penetrate through the container itself.

In a further advantageous embodiment, the radiation device radiates the light onto the container along a longitudinal direction thereof, for example from above.

As mentioned above, the labels or bottles themselves also reflect their surroundings. Since these bottles still have curvatures, any undesired mirror effects are enhanced in this way. For this reason, a high radiation of light from above is preferably used (radiation from below is also possible), and this light is emitted onto the bottle to be inspected by means of light emitting diodes emitting a narrow beam and is preferably also concentrated by means of Fresnel lenses. In this way, the creation of mirror images of the surroundings and of neighboring bottles on the bottle will be kept to a minimum. A certain proportion of scattered light will advantageously be distributed within the housing and will generate a light which will be used for localizing the containers. In this way, the high dynamics of the image capturing device will preferably be used. The actual inspection of the containers will be carried out with a lot of light in the upper grey scales, and the determination of the bottle contour will be achieved with little light (dim light) in the lower grey scales.

In a further advantageous embodiment, the device comprises a housing which essentially completely surrounds the image capturing device and the container to be monitored and the background forms part of this housing. Thus, preferably the entire device is located within the mentioned housing, so that it becomes possible to even avoid any interfering light effects from the outside. Advantageously, the device has a plurality of image capturing devices disposed in a circumferential direction around the container. In a preferred embodiment, a total of four image capturing devices are provided, which are uniformly disposed in the circumferential direction around the container and which monitor the container in each case transversely to the longitudinal axis or at a slight angle relative to this direction.

In a further preferred embodiment, the housing has a cover surface facing in the direction of the container, and this cover surface, has both lighter and darker areas.

It would also be desirable to design the housing in such a way that it is not too high, in order to save material. For this reason, also the top of this housing is provided with a light and dark or a black and white pattern, which continues the coloring of the lateral walls in such a way that the perspective remains correct. This will be explained in more detail with reference to the figures.

In a further advantageous embodiment, a lens body is provided between the radiation device and the container. In this way, a uniform illumination of the entire bottle is achieved. By means of the combination of using LEDs emitting narrow beams and the Fresnel lenses mentioned, the light will be directed onto the bottle to be monitored without any interference from the neighboring bottles. The light of the comparatively large LED surface which is preferably at least 100 mm×100 mm, particularly preferably at least 200 mm×200 mm and especially preferably at least 300 mm×300 mm, is focused by said Fresnel lens onto the transporting device or the conveyor belt. In this area, the light is concentrated onto a circular surface of approx. 100 mm in diameter. In this way, the quadratic decrease of the illumination strength is partially compensated by the distance from the radiation device, so that a more uniform illumination along the height of the bottle is achieved.

By means of varying the brightness of the LED field, the illumination may be made even more homogenous. In a preferred embodiment, a square frame having four large LED modules as well as two smaller LED modules at the centre are used, which, however, are at least partially switched off or are adjusted to be darker.

Preferably, the lens body which is particularly preferably a Fresnel lens, has a focal length of approx. 400 mm and a diameter in the order of 300-400 mm. The lens may, if necessary, also have a quadrangular shape. The light of the LED module is directed onto the container through the lens in a cone-shaped pattern and thus allows a uniform 360° illumination. Due to the illumination surface being markedly larger by comparison with the container diameter, and due to the illumination coming at an angle from the outside, any interfering shadow casting on the cylindrical container area is advantageously avoided.

In a further advantageous embodiment, the lighter areas of the background are disposed in the corner areas of the housing. Also the image capturing devices are preferably disposed in the corners of the housing. Thus, preferably, each image capturing device is surrounded by a lighter background which, however, is used in each case for accommodating the image capturing device located opposite thereto.

In a further advantageous embodiment, the housing has a inlet area and an outlet area for the containers, and these areas are disposed in dark areas of the background. Any light entering from the outside could be refracted or scattered by the bottles and/or the conveyor belt in an interfering manner. Therefore, dark tunnels are provided at the entrance and the exit of the device, since a light entrance/exit would make the bottle contour look lighter again.

Preferably, the background surfaces are higher than the bottle itself. The bottles are partially viewed also in an oblique direction, and additionally many bottles have spheroidal constrictions. In this way, the light is deflected not only laterally, but also vertically. For this reason it is advantageous to design said background surfaces to be higher than the bottles and preferably at least twice as high as the bottles. Preferably, the bottle is positioned approximately halfway between the camera and the background. Towards the bottom relative to the bottle, there is usually sufficient room available, and besides, the bottles are normally designed cylindrically in this area, so that it is sufficient to start the lateral walls of the housing below the transport device.

The background, with the exception of the light-dark contrasts mentioned, is preferably without a contour. As mentioned above, it is possible in the case of light and dark bottles to look through these. In order to keep any interferences resulting therefrom at a minimum for the evaluation, the housing or the background is preferably designed to be without a structure in as far as possible, i.e. to be without a structure except for the mentioned black and white pattern for determining the contour. In this way, a largely homogenous background is achieved and said corners of the housing are always behind the container in the image and will not interfere with the determination of the contour.

As mentioned, however, the image capturing devices are positioned in the corners. This means that in this area, the housing has at least openings which may cause interference during image capturing. For this reason, the image capturing devices will preferably view the bottles or containers through small holes in the housing and are obscured behind white objective housings. These holes may be detected as minor interferences at least once in light bottles. Preferably, however, these especially localized interferences are compensated using suitable software.

Instead of a square housing, it would also be possible to design the housing to be round and, again, to dispose the image capturing devices in the circumferential direction around the containers.

In a further advantageous embodiment, the radiation device has a pulsed light source. This is used both for generating the light and for capturing pulsed events, or the containers are each viewed using a flashlight.

The present invention further relates to a process for inspecting the external surfaces of containers, wherein the containers to be inspected are transported by means of a transport device, are illuminated by means of a radiation device and the container illuminated by the radiation device is captured by means of an image capturing device, said capturing device outputting a spatially resolved image of the light captured or the surface of the container.

According to the invention, a background is positioned behind the container with respect to the image capturing device, said background having at least one lighter area and at least one darker area with respect to this lighter area. The darker areas are here disposed in the transporting direction and transversely thereto. The darker zones are preferably displaced by 45° in relation to the monitoring devices.

BRIEF SUMMARY OF THE DRAWINGS

Further advantages and embodiments will become evident from the attached drawings, wherein.

DETAILED DESCRIPTION OF THE INVENTION

Figure 1:
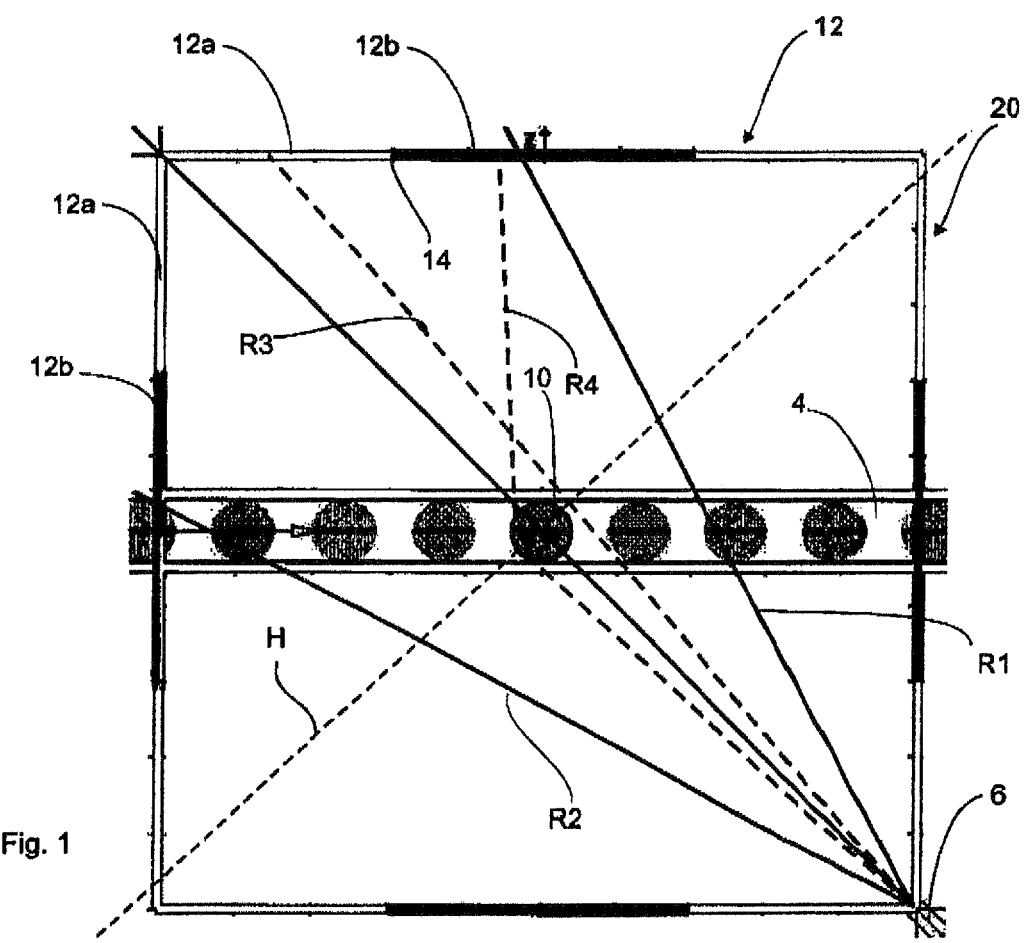
FIG. 1 shows a schematic view for illustrating the invention.

FIG. 1 shows a schematic view for illustrating the invention. This illustration only shows one image capturing device 6 which accommodates a bottle 10 to be inspected. The radiation device is not shown in FIG. 1. Reference numeral 20 relates to a housing having a background identified in its entirety with 12, which is positioned behind the container 10 in the viewing direction of the image capturing device 6. The image capturing device 6 is here capable of monitoring the area defined by the edges R1 and R2.

Thus, the image capturing device 6 captures both the lighter area 12a of the background 12 and the darker area 12b of the background 12. In a section of contrast 14, the lighter area 12a merges into the darker area. When a dark container is viewed, this darker container contrasts with the light and preferably white area 12a of the background 12 which lies behind it. If a light container containing a light liquid is used, the image capturing device 6, however, also views the black background areas through the container, however, outside thereof there are light areas again, so that owing to this contrast, the contour of the bottle may be determined. If a light bottle containing a light liquid is viewed, the light areas of the background 12a are visible to the left and the right of the bottle, and at the sides of the bottle, refractions so strong that the respectively dark background portions become visible will occur.

Reference numeral H relates to a dashed line for illustrating the geometrical relationships. This dashed line H extends vertically to the main viewing direction of the image capturing device 6. The section of the background 12, which is located behind the dashed line H if viewed from the image capturing device 6, is regarded as the area of the background 12, which lies behind the container.

Figure 2:
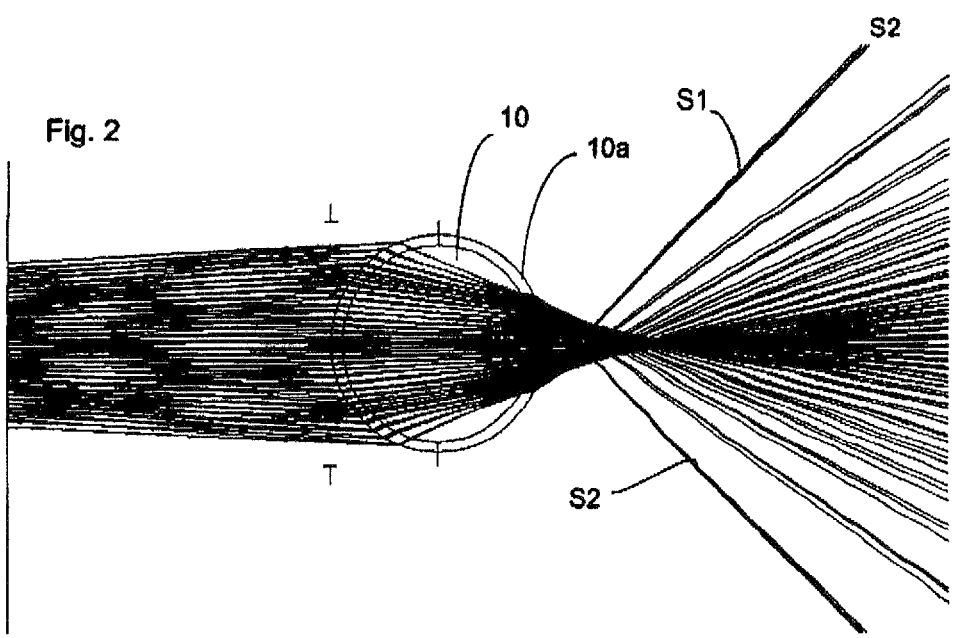
FIG. 2 shows an illustration of a beam path through a container to be inspected.

FIG. 2 illustrates the beam paths through a container or a bottle 10. It can be seen that the outer beam portions S1 and S2 are particularly severely refracted at the sides 10a of the container 10, so that in this way, the dark background areas 12b (FIG. 1) are visible through the bottle. The more central areas of the containers, however, are not refracted in the same extreme way, so that in this area, only the light background area 12a can be detected. Thus, the edge contours of the container may be determined very exactly by the strips mentioned.

In FIG. 1, two beams R3 and R4 are shown for illustration. The beam path R3 runs just past the container 10, so that the image capturing device will capture a lighter area 12a of the background 12 here. The beam R4 is refracted on the container 10 so strongly that a dark background 12b of the background 12 will be captured here by the image capturing device 6. Thus, the filled container acts like a cylindrical lens.

Figure 3:
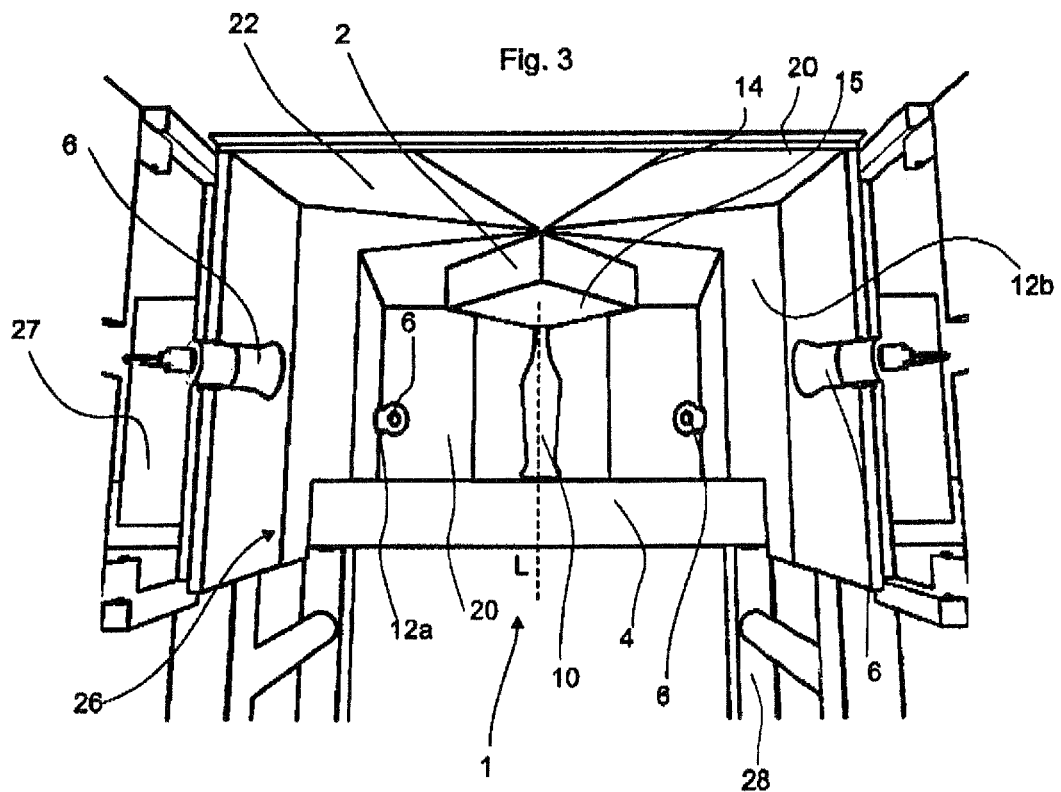
FIG. 3 shows a perspective view of a device according to the invention.

FIG. 3 shows a first perspective view of a device 1 according to the invention. Here, again, the housing 20 may be seen, which has a cover 22. In the four corners of the housing 20, the four image capturing devices 6 are provided. Reference numeral 2 relates here to a radiation device which illuminates the container 10 from above in the longitudinal direction L of the container. Here, this radiation device 2 has a square cross section, which is twisted by 45° with respect to the running direction of a conveyor belt 4 on which the bottles are conveyed here from the left to the right. Typically, the labels to be monitored are lightest in the centre of the image and become darker towards the edge of the bottle, despite a uniform illumination.

This effect is moderated, since in the direction of the side of the container 10, the corners of the square radiation device 2, each of which protrudes outwards, are located. It is further achieved that the individual image capturing devices no longer view in the direction of the corners of the radiation device 2, but towards the respective (located further away) centre of the sides. In this way it is achieved that the opposite corner no longer protrudes into the image of said image capturing device 6.

Further, the radiation device has a lens, in particular a Fresnel lens 15. As an alternative to this Fresnel lens with the LED modules, it would also be possible to orientate each individual LED in the radiation device in a corresponding manner, which, however, is more complicated from a manufacturing point of view. Due to the arrangement of the Fresnel lens it becomes possible to produce a very special radiation device 2 with prefabricated simple components.

It can be seen that the housing has white background areas 12a in each of its corners. In each of the areas between the corners there are black areas 12b of the background. These areas also extend into the cover 22 of the device, where these black areas are tapered towards the centre and form in this way the approximate shape of a Maltese cross when viewed from the top. Reference numeral 26 relates to an inlet for the transport device 4 which is also disposed in the area of the dark background 12b. Outside of the housing 22, there is a tunnel 27 which assists in making the inside of the housing darker. Reference numeral 28 relates to a carrier for the device 1.

Figure 4:
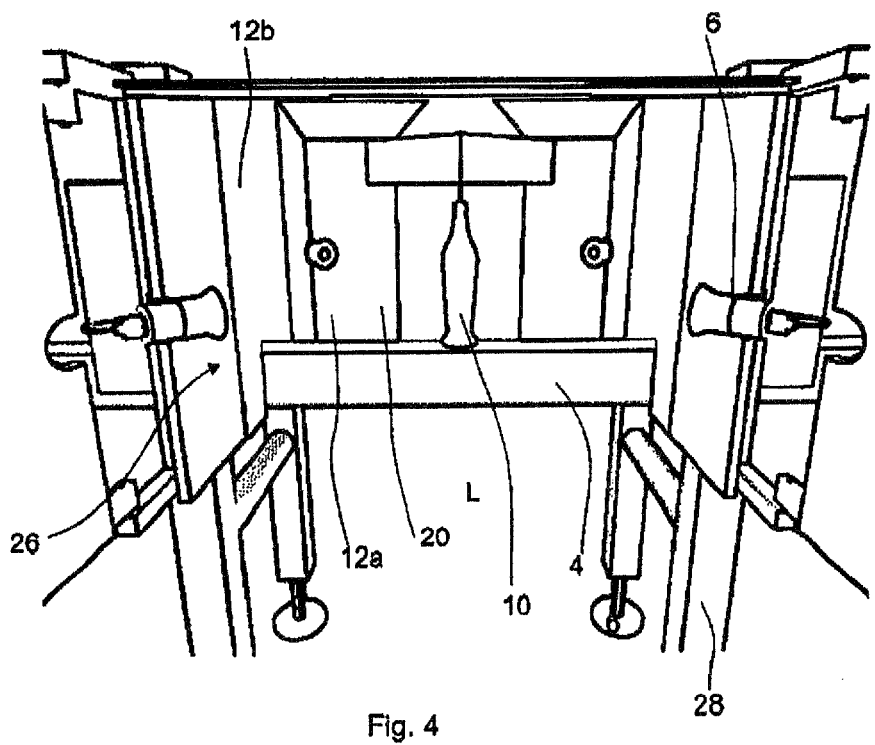
FIG. 4 shows a further perspective view of a device according to the invention.

FIG. 4 shows a further view of a device 1 according to the invention. Here, too, it can be seen that darker areas 12b of the background are disposed in each case at the entrance and the exit of the transport device 4 and lighter areas are disposed in the respective corners. Contrary to the prior art, therefore, the internal space of the housing 22 is formed neither as a black internal space nor as a homogenous light internal space. Rather, a defined internal space is suggested which is designed in a more advantageous manner for the inspection task given here, as known spaces. For label inspection, an illumination orientated parallel to the bottle axis L instead of a diffuse illumination is provided. The illumination therefore illuminates at a flat angle from above and/or from below the surface of the container 10. The flat angle allows reflection-free camera images to be obtained.

The image capturing device is disposed essentially vertically relative to the bottle axis L. Preferably, the illumination is designed in such a way that the course of intensities relative to the bottle height remains the same, but it may also have a gradient. Preferably, however, it is achieved that the container 10 is illuminated around the circumference uniformly at the same height. Depending on the circumstances it may occur that surfaces having a certain inclination (angle of incidence of the illumination=angle of exit of the camera) mirror the lamp in the camera image. Here, the viewing direction of the image capturing device may be changed. If it is changed, for example by means of a second camera which is to be seen as complementary to the first, this effect is avoided. The second camera will then no longer be orientated vertically relative to the container axis L.

Compared to a diffuse illumination, a further advantage lies in the fact that the respective neighboring containers neither interfere with the illumination of the container 10 to be inspected nor influence, in the case of a diffuse illumination of the neighboring container, the lighting conditions on the container to be inspected.

Figure 5:
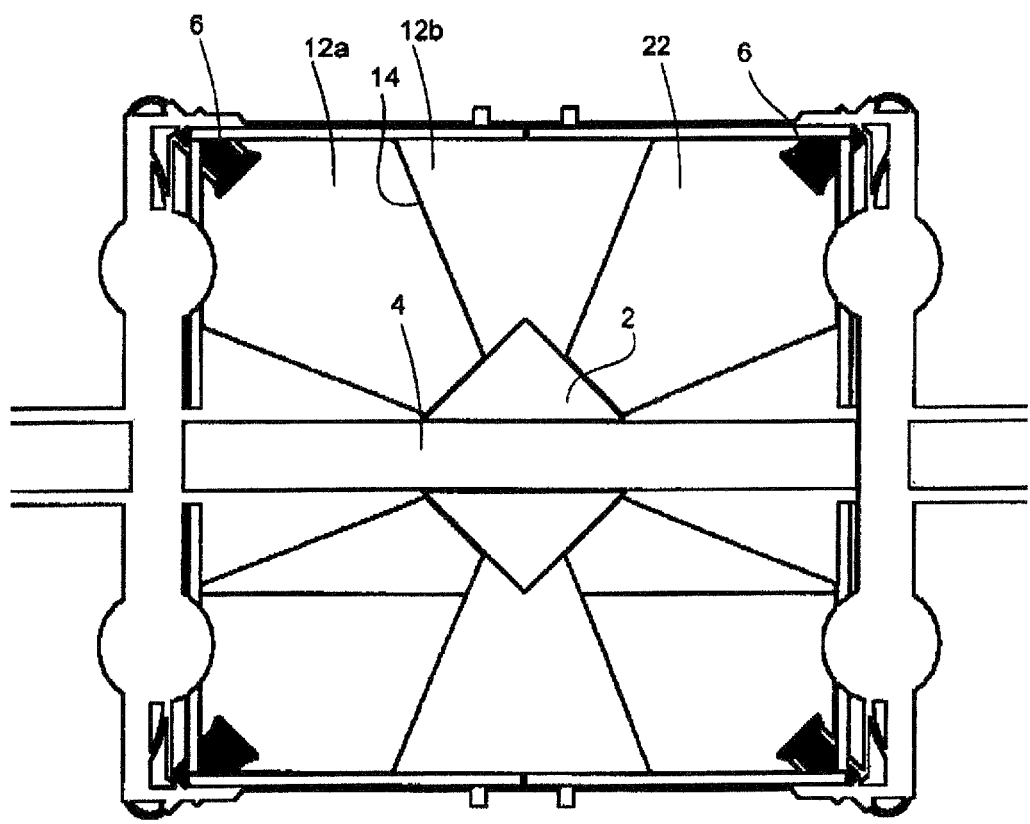
FIG. 5 shows a top view onto a device according to the invention from below.

FIG. 5 shows a top view of the device according to the invention from below. What can be seen here in particular is the cover 22 of the device, which also has light areas 12a and dark areas 12b. It can also be seen here that the viewing area of the housing, which lies opposite the image capturing device, is at least partially lined to be light. The question about the optical properties is of secondary importance in this case. More precisely, any preferred reflection properties or diffusion properties are not necessarily required. It is sufficient here to be able to detect the contour of the dark bottles.

The background surface may thus have a colour or may also be white. As mentioned above, however, rotationally symmetric light products, such as the filled bottles shown here, act like a cylindrical lens. The view through the transparent clear container is deflected according to optical law and will no longer fall on the lighter area of light, but on an area which is darker. In this way, the side of the container will appear dark, as described above.

The image capturing devices are preferably, as shown in FIG. 5, distributed in a symmetrical manner. Thus, the respectively opposite area of the camera is lined to be light, the areas to the left and the right thereof to be dark. The light areas are not needed to illuminate the container or the labels thereof on the camera side, but to detect the contour of the container according to the transmitted light technique. Thus, in order to provide a comprehensive solution, i.e. for light and dark areas (whilst the combination of container material and filled product has to be considered in each case), additional dark areas are provided in a suitable position, and these are formed only partially in the lateral housing or they extend beyond the lateral housing onto the cover 22 or the bottom of the housing. In the case of several partial images of a container, which are offset around the circumference, the position and the size of the container images may be accurately detected in each case via the clearly defined contours and, independent from any random positional or dimensional tolerances of the individual containers on a conveyor, may be combined into a precise panorama picture which can now be evaluated for inspecting the label or the like.

All of the features disclosed in the application documents are claimed as essential to the invention, in as far as they are novel over the prior art either individually or in combination.

The invention claimed is:

1. A device for inspecting the external surfaces of containers, including a radiation device adapted to radiate light onto a container to be inspected, along a longitudinal direction thereof, including a transport device which transports the container with respect to the radiation device, and including an image capturing device adapted to capture an image of the container illuminated by the radiation device, with a background disposed in a geometrical area, which is detected by the image capturing device, behind the container, with respect to which the container is imaged, wherein the background has at least one lighter area and one darker area by comparison to said lighter area, wherein the area of the background, which lies behind the container in the viewing direction of the image capturing device, is a lighter area, and, wherein the background has a section of contrast, in which the lighter area merges into the darker area, and the device has a housing which completely surrounds the image capturing device and the container to be monitored, and the background forms part of said housing, and wherein a radiation device is mounted within and on said housing and the radiation device illuminates the container from above in a longitudinal direction (L) of the container.

2. The device as claimed in claim 1, wherein an area of contrast between the lighter area and the darker area extends vertically.

3. The device as claimed in claim 1, wherein a darker area of the background follows a lighter area of the background on both sides.

4. The device as claimed in claim 1, wherein the radiation device radiates the light onto the container along a longitudinal direction (L) thereof.

5. The device as claimed in claim 1, wherein the image capturing device views the container vertically relative to the longitudinal direction (L) of the container.

6. The device as claimed in claim 1, wherein the device has a plurality of image capturing devices disposed in the circumferential direction around the container.

7. The device as claimed in claim 6, wherein the housing has a cover surface facing in the direction of the container, and this cover surface has both lighter and darker areas.

8. The device as claimed in claim 1, wherein the housing has a cover facing in the direction of the container, and this cover has both lighter and darker areas.

9. The device as claimed in claim 1, wherein a lens body is provided between the radiation device and the container.

10. The device as claimed in claim 1, wherein the lighter areas of the background are each disposed in the housing essentially opposite the image capturing devices in the viewing direction.

11. The device according to claim 10, wherein the housing comprises an angularly shaped housing, and lighter areas of the background are each disposed in the housing in the corner areas thereof.

12. The device as claimed in claim 1, wherein the housing has an inlet area for the containers and this inlet area is disposed in a darker area of the background.

13. The device as claimed in claim 1, wherein the radiation device has a pulsed light source.

14. A method for inspecting external surfaces of containers, using the device as claimed in claim 1 wherein the containers to be inspected are transported using a transport device, are illuminated using a radiation device adapted to radiate light onto the container along a longitudinal direction thereof, and the container illuminated by the radiation device is captured using an image capturing device, said capturing device outputting a spatially resolved image of the captured light, wherein a background is located in a geometrical area, which is detected by an image capturing device, behind the container—said background having at least one lighter area and one or more darker area(s) by comparison to said lighter area, wherein the image capturing device is adapted to detect the radiation directed by the radiation device onto the container and scattered from said container, and wherein capturing of radiation reflected from the container by the image capturing device is avoided, and, wherein the background has a section of contrast, in which the lighter area merges into the darker area.

15. The method as claimed in claim 14, wherein in the case of lighter containers, a contour of a container is made to be visibly defined in front of the darker areas, and the exact position and size of the container are determined therefrom, in particular for an accurate composition of a panorama image from several partial views of a container, which is then inspected and evaluated.

16. The device according to claim 1, wherein the background comprises a first region, which is arranged behind the container along a straight line which runs from the image capturing device through the longitudinal direction of the container.

17. The device according to claim 16, wherein the first region is observable by the image capturing device on a left and a right side of the container.

18. The device according to claim 1, wherein the section of contrast is an edge or a line in which the lighter area merges into the darker area.

19. The device according to claim 1, wherein the darker areas are disposed in such a way, that the light emitting therefrom can still be seen when monitoring the bottle.

20. The device according to claim 1, wherein the transport device comprises a conveyor belt.

21. The device according to claim 1, wherein the radiation device has a Fresnel lens.

22. The device as claimed in claim 1, wherein the light radiation device is mounted on said cover.

23. A device for inspecting the external surfaces of containers, including a radiation device adapted to radiate light onto a container to be inspected, along a longitudinal direction thereof, including a transport device which transports the container with respect to the radiation device, and including an image adapted to capture device capturing an image of the container illuminated by the radiation device, with a background disposed in a geometrical area, which is detected by the image capturing device, behind the container with respect to which the container is imaged, wherein the background has at least one lighter area and one darker area by comparison to said lighter area, and, wherein the radiation device radiates the light onto the container along a longitudinal direction (L) thereof, and, wherein the background has a section of contrast, in which the lighter area merges into the darker area, and the device has a housing which completely surrounds the image capturing device and the container to be monitored and the background forms part of said housing, and wherein a radiation device is mounted within and on said housing and the radiation device illuminates the container from above in the longitudinal direction (L) of the container.

* * * * *